(12) United States Patent
Kobayashi (10) Patent No.: US 8,528,544 B2
(45) Date of Patent: Sep. 10, 2013

(54) INHALER

(75) Inventor: Masaya Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1160 days.

(21) Appl. No.: 12/125,579

(22) Filed: May 22, 2008

(65) Prior Publication Data
US 2008/0295827 A1 Dec. 4, 2008

(30) Foreign Application Priority Data

May 30, 2007 (JP) ................. 2007-142808
May 8, 2008 (JP) ................. 2008-121816

(51) Int. Cl.
B05B 7/00 (2006.01)
A61M 15/00 (2006.01)
A61M 16/00 (2006.01)
A61M 11/00 (2006.01)

(52) U.S. Cl.
USPC ............ 128/200.19; 128/200.14; 128/200.11

(58) Field of Classification Search
USPC ........... 128/200.19, 200.11, 200.14; 261/78; 604/94.01, 212, 264
See application file for complete search history.

(56) References Cited

U.S. PATENT DOCUMENTS

| | | | | |
|---|---|---|---|---|
| 5,178,138 A * | 1/1993 | Walstrom et al. | ........ | 128/200.23 |
| 5,727,546 A * | 3/1998 | Clarke et al. | ............ | 128/203.15 |
| 5,894,841 A * | 4/1999 | Voges | ...................... | 128/203.12 |
| 6,196,218 B1 * | 3/2001 | Voges | ...................... | 128/200.14 |
| 6,443,146 B1 * | 9/2002 | Voges | ...................... | 128/200.14 |
| 6,684,880 B2 | 2/2004 | Trueba | | |
| 7,073,499 B1 * | 7/2006 | Reinhold et al. | ......... | 128/200.18 |
| 7,513,253 B2 | 4/2009 | Kobayashi et al. | ...... | 128/203.21 |
| 8,082,917 B2 * | 12/2011 | Ooida | ........................ | 128/200.14 |
| 8,201,554 B2 * | 6/2012 | Reinhold et al. | ......... | 128/200.16 |
| 8,365,725 B2 * | 2/2013 | King et al. | ............... | 128/203.15 |
| 2003/0101991 A1 * | 6/2003 | Trueba | ..................... | 128/200.14 |
| 2004/0107961 A1 * | 6/2004 | Trueba | ..................... | 128/200.16 |
| 2006/0081239 A1 * | 4/2006 | Alley et al. | ............... | 128/200.14 |
| 2006/0174869 A1 * | 8/2006 | Gumaste et al. | ......... | 128/200.14 |
| 2007/0240706 A1 | 10/2007 | Kobayashi et al. | ...... | 128/200.14 |
| 2007/0240712 A1 * | 10/2007 | Fleming et al. | .......... | 128/203.15 |
| 2007/0240714 A1 * | 10/2007 | Dunne et al. | .............. | 128/203.15 |
| 2008/0092888 A1 * | 4/2008 | Haroutunian | ............ | 128/203.29 |

(Continued)

FOREIGN PATENT DOCUMENTS

JP  08511966 A  12/1996
JP  2004290592 A  10/2004

(Continued)

*Primary Examiner* — Loan Thanh
*Assistant Examiner* — Shila Jalalzadeh Abyane
(74) *Attorney, Agent, or Firm* — Fitzpatrick, Cella, Harper & Scinto (57) ABSTRACT

The present invention prevents liquid droplets from colliding with each other and prevents changes in the liquid droplet size, and prevents degeneration of medicinal solutions from occurring in the center portion where the flow rate of the airflow is maximum inside the airflow path. Inside an inhalation flow path of a flow path mouthpiece unit having a mouthpiece at one end, a cylindrical structure is disposed, and the cross-section of the inhalation flow path is made ring-shaped. The surface of the structure is provided with medicine ejection portions, and the medicinal liquids are supplied from a reservoir provided inside the structure. Even when the medicine ejection portions are simultaneously driven, this structure prevents the liquid droplets from colliding with each other to change the liquid droplet size and the like.

10 Claims, 12 Drawing Sheets

(56) References Cited

U.S. PATENT DOCUMENTS

| | | | |
|---|---|---|---|
| 2008/0115784 A1* | 5/2008 | Gumaste et al. | 128/203.15 |
| 2008/0202514 A1* | 8/2008 | Kriksunov et al. | 128/203.15 |
| 2009/0283094 A1* | 11/2009 | Hamano et al. | 128/203.15 |
| 2010/0229860 A1* | 9/2010 | Gumaste et al. | 128/203.15 |
| 2012/0222675 A1* | 9/2012 | Dunne et al. | 128/203.15 |

FOREIGN PATENT DOCUMENTS

| | | |
|---|---|---|
| WO | 02/05898 A1 | 1/2002 |
| WO | 2004/007346 A2 | 1/2004 |
| WO | 2004/011069 A1 | 2/2004 |
| WO | 2004/011070 A1 | 2/2004 |
| WO | 2004/011071 A1 | 5/2004 |

* cited by examiner

AIR INLET

INHALER

BACKGROUND OF THE INVENTION

1. Field of the Invention

The present invention relates to an inhaler for changing a liquid and the like containing an active ingredient used for respiratory disease treatment into liquid droplets, thereby allowing a user to inhale the same.

2. Description of the Related Art

As one of the methods for changing a liquid sample to fine liquid droplets and ejecting the same, an ink jet technique is publicly known. The ink jet system has a feature of showing high controllability even when the liquid amount being changed to liquid droplets and ejected is infinitesimal. Types of fine liquid droplet ejection of this ink jet system include a vibration system using a piezoelectric element and the like, and a thermal ink jet system using a micro-heater element. In the thermal ink jet system, reduction of the size of the micro-heater element is relatively easy, and as compared with the vibration system using the piezoelectric element and the like, the number of ejection ports provided per unit area can be increased. Further, the cost required for its manufacture can be significantly reduced.

Many spray apparatuses are adapted to spray a plurality of substances instead of a single composition. Such spray apparatuses are variously used to spray medicine and an auxiliary substance, a plurality of medicines, and the like, and a wide range of medicines are also used such as compounds for disease treatment, fragrant materials, and coloring materials.

Heretofore, when spraying a plurality of materials, a plurality of materials are mixed to complete the ejection in a single operation. However, this has often caused troubles. Even the materials which are stable individually may change in their states and natures when they coexist with other materials under the same atmosphere. Reasons for such a phenomenon may include interactions between ions or due to an electrical charge, interactions for releasing hydrogen bonding, and actions and the like accompanied by π-conjugation. Further, there are various combinations, and this pot life is sustained over a long period in some combinations and is shorter in other combinations.

When spraying the plurality of materials, a mechanism for mixing the liquids immediately before spraying, which is often found in the conventional spraying method, causes liquid droplets to collide with each other, causing the droplets to become large in size or diameter, and does not produce fine liquid droplets. Further, there remains a problem that the amount thereof is unable to be accurately controlled (see WO2002/05898 and WO2004/007346).

While an example of ejecting a plurality of kinds of medicinal solutions is found in the ink jet system, there is no disclosure made on a specific configuration for the mechanism to prevent the collision of the liquid droplets (see U.S. Pat. No. 6,684,880).

Further, there is an inhaler, in which two medicines not storable in one canister in the inhaler of an aerosol system are stored in respective separate canisters, thereby allowing a plurality of medicines to be inhaled by a user (see WO2004/011069, WO2004/011070, and WO2004/011071).

SUMMARY OF THE INVENTION

When a liquid medicine is ejected into an airflow path connected to a suction port (or a mouthpiece) and this is inhaled by the user, ejecting the liquids from a plurality of ejection heads in one inhalation may cause the liquid droplets to collide with each other in the flow path. Usually, the flow rate of the airflow inside the flow path is the lowest near the outer wall of the flow path, and is the highest in the center portion of the flow path, and therefore, even when the liquids are ejected from a plurality of locations, the liquid droplets are concentrated in the center portion of the flow path, and as a result, in the center portion where the flow rate of the airflow becomes the highest, the liquid droplets end up in colliding with each other. Different medicinal solutions to be inhaled have different sites where they are desired to be deposited inside the lung, and therefore, a preferable liquid droplet size is predefined. Consequently, the change in the liquid droplet size due to the collision of the liquid droplets is not preferable. Further, when heterogeneous medicinal solutions are ejected, the collision of the medicinal solution droplets may cause the modification of the medicinal solutions.

An object of the present invention is to provide an inhaler capable of controlling a liquid droplet amount sprayed in the airflow with high accuracy and further capable of preventing the liquid droplet size from becoming large due to the collision of the liquid droplets ejected in an inhaling apparatus and the like used for medical purposes.

In view of the above described object, the inhaler of the present invention is an inhaler for ejecting a medicine to allow a user to inhale the medicine and includes a suction port for the user to inhale the medicine, an airflow path whose one end is connected to the suction port and other end has an air inlet and guiding the medicine to the suction port by an airflow generated by the inhalation by the user, a plurality of medicine ejection portions for ejecting the medicine to the airflow path, and a structure inside the airflow path.

By disposing the structure inside the airflow path, the ejected liquid droplets can be prevented from colliding with each other and becoming large in liquid droplet size, even when the liquids are simultaneously ejected from the plurality of medicine ejection portions.

Hence, in each spraying operation, the medicines usable for a plurality of medical treatment purposes can be administered with good reproducibility at a predetermined concentration, while being controlled to an arbitrary ratio with high accuracy.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 3A and 3B illustrate flow path mouthpiece units only of the inhaler of FIG. 1.

FIGS. 4A, 4B and 4C illustrate rectangular flow path mouthpiece units according to a second embodiment.

FIGS. 5A, 5B, 5C and 5D illustrate C-flow path mouthpiece units according to a third embodiment.

FIGS. 6A and 6B illustrate the flow path mouthpiece units according to a fourth embodiment.

FIGS. 7A and 7B illustrate the flow path mouthpiece units according to a fifth embodiment.

FIGS. 8A, 8B and 8C illustrate the flow path mouthpiece units according to a sixth embodiment.

FIGS. 9A, 9B and 9C illustrate the flow path mouthpiece units according to a seventh embodiment.

FIGS. 10A and 10B illustrate the flow path mouthpiece units according to an eighth embodiment.

FIGS. 11A and 11B are schematic cross-sectional views of the airflow direction of an airflow path. An arrow from an ejection head 6 represents a moving direction of an ejected liquid droplet, and a sold line inside the airflow path is a line imaging the flow rate distribution of the airflow.

DESCRIPTION OF THE PREFERRED EMBODIMENTS

Preferred embodiments of the present invention will now be described in detail in accordance with the accompanying drawings.

Figure 1:
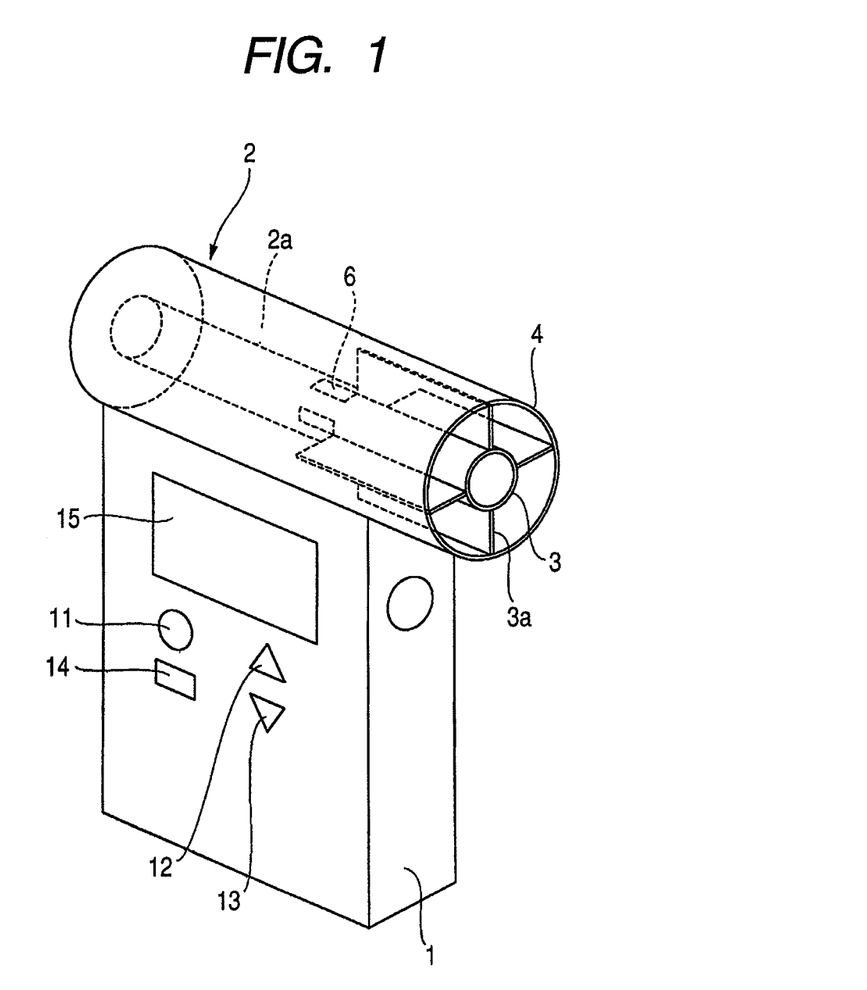
FIG. 1 is an exterior perspective view illustrating a first embodiment.
Figure 2:
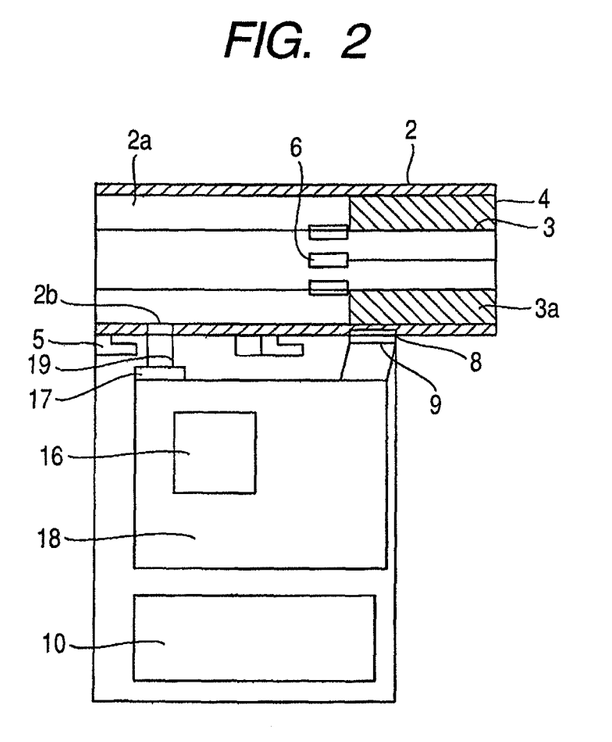
FIG. 2 is a cross-sectional view illustrating an inhaler of FIG. 1.

FIGS. 1 and 2 are an exterior perspective view and a cross-sectional view illustrating a first embodiment, respectively. This is a portable inhaler, and is provided with a flow path mouthpiece unit 2 on a housing case 1. One end of the flow path mouthpiece unit 2 is provided with a mouthpiece 4 serving as a suction port, and the other end serves as an air inlet so that the airflow is generated in a space (hereinafter, referred to as an airflow path) inside the flow path mouthpiece unit 2 when the user inhales. Inside the flow path mouthpiece unit 2, a structure 3 is held by a support 3a. The side surface of the flow path mouthpiece unit 2 is provided with a hook claw 5 for connecting the mouthpiece unit to the housing case 1. The surface of the structure 3 is provided with a plurality of ejection heads 6, and inside the structure 3, there is provided a reservoir 7 (see FIG. 3A) serving as a container for storing a medicinal solution ejected from the ejection head 6. The reservoir 7 is communicated with the ejection head 6 to supply the medicine to the ejection head 6. The flow path mouthpiece unit 2 has an electrical connection surface 8, and supplies the power through an electrical connection member 9 disposed in the housing case 1.

The user holds a mouthpiece (suction port) 4 of the flow path mouthpiece unit 2 in his mouth. The housing case 1 is provided with components such as a battery 10, a menu changeover button 11, a setting up button 12, a down button 13, and a SET button 14, which allow the user to perform the setting, and a display unit 15 for displaying a dose amount, time, and an error.

An arithmetic circuit and memory 16 is provided on a control substrate 18, and saves data such as a liquid ejection condition, an ejection amount, and time. The power for driving these elements may be from a secondary battery and is supplied from a rechargeable battery 10.

Further, to effectively accomplish the inhaling of the medicine, the inhalation by the user and the ejection of the liquid droplets are preferably synchronized. Hence, to detect the inhalation by the user and start the ejection based on an inhalation detecting signal, a pressure sensor 17 is provided on the control substrate 18 as an inhalation detecting sensor. The pressure sensor 17 detects a negative pressure generated inside the flow path by the inhalation by the user. The flow path mouthpiece unit 2 is provided with a communication hole 2b in communication with an inhalation flow path 2a, and the communication hole 2b is communicated with the pressure sensor 17 through a pressure detection tube 19.

Figure 11A:
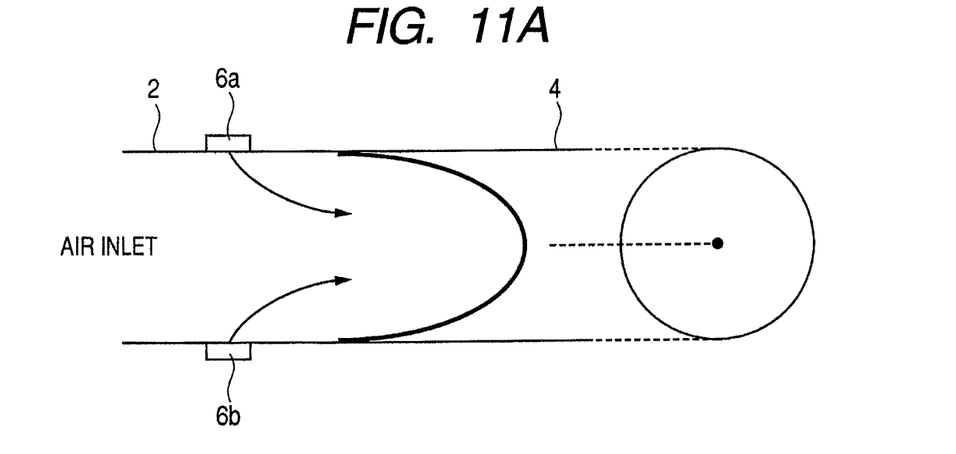
FIG. 11A is a cross-sectional view schematically illustrating the movement of the liquid droplet inside the conventional airflow path having no structure 3.

By providing such a structure 3 inside the airflow path, the likelihood of the liquid droplets ejected from the plurality of ejection heads colliding with each other can be reduced. This point will be described by using FIGS. 11A and 11B. FIG. 11A schematically illustrates a cross-sectional view of the conventional airflow path having no structure 3 inside the airflow path. In this case, the flow rate of the airflow generated by the inhalation by the user is low near the inner wall of the flow path mouthpiece unit 2, and is the highest near the center of the airflow path. The bold line inside the airflow path in the figure shows this fact as an image. The view on the right side of FIG. 11A is a cross-sectional view of the airflow path, and a center point represents the highest point in flow rate of the airflow. Here, when the medicine is ejected from the plurality of ejection heads, the liquid droplets ejected as indicated by the arrow in the figure are liable to concentrate together near the center of the airflow path, and there is likelihood that the liquid droplets end up in colliding with each other before reaching the mouthpiece.

Figure 11B:
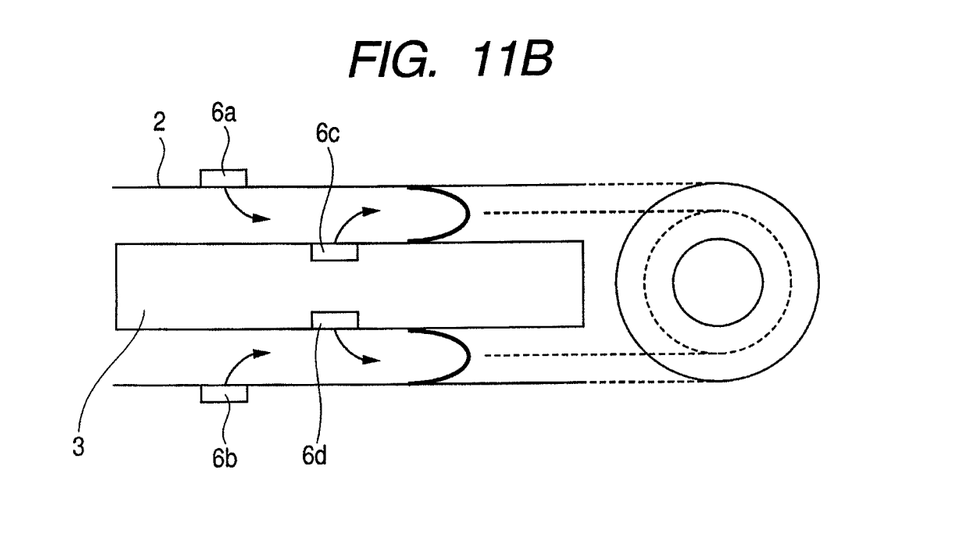
FIG. 11B is a cross-sectional view schematically illustrating the movement of the liquid droplet inside the airflow path of the present embodiment having the structure 3.

On the other hand, FIG. 11B is a cross-sectional view of the airflow path provided with the structure 3 of the present invention. In this case, the flow rate of the airflow generated by the inhalation by the user does not have its maximum point concentrated on one point. That is, the airflow becomes slow on the surface of the structure 3 and the inner wall surface of the flow path mouthpiece unit 2, and becomes the highest near the intermediate point thereof. The bold line inside the airflow path in the figure shows this fact as an image. The view on the right side of FIG. 11B is a cross-sectional view of the airflow path, and a portion indicated by a dotted line is a place where the flow rate of the airflow is the highest. Here, if medicines are ejected from the plurality of ejection heads, liquid droplets would concentrate in the vicinity of the respective nearest locations of the location ejected, from among the locations where the flow rate becomes the maximum. This can reduce probabilities of collision of the liquid droplets ejected from the plurality of ejection heads. This holds true, as illustrated, in the case where the plurality of ejection heads is provided inside the structure 3 and in the case where they are provided in the inner wall of the flow path mouthpiece unit 2.

Thus, the structure 3 of the present invention is a structure of such a shape that the maximal point of the flow rate of the airflow does not gather at one point, but can be dispersed.

Figure 3A:
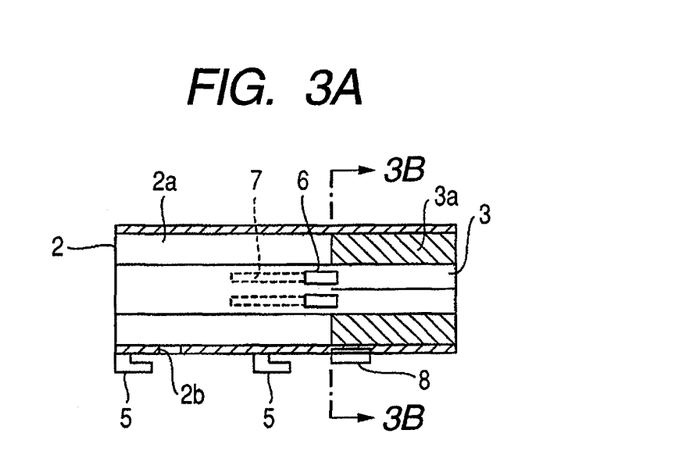
FIG. 3A is a cross-sectional view in an axial direction.
Figure 3B:
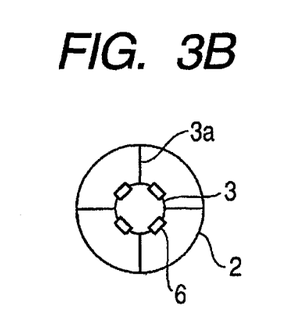
FIG. 3B is a cross-sectional view seen from the line 3B-3B of FIG. 3A.

FIGS. 3A and 3B illustrate only the flow path mouthpiece unit 2, and FIG. 3A is a cross-sectional view in the axial direction of the flow path mouthpiece unit 2, and FIG. 3B is a cross-sectional view seen from the line 3B-3B of FIG. 3A. The bottom of the mouthpiece unit is provided with a hook claw 5 for connecting the unit to the housing case 1. In consideration of the usability of the flow path mouthpiece unit 2 in applying and removing, the structure of the hook claw 5 is desirably simple. Further, the mouthpiece unit has an electrical connection surface 8 for supplying the power to each ejection head 6 through the support 3a of the structure 3. The ring-shaped airflow path 2a of the flow path mouthpiece unit 2 with the provision of the structure 3 needs not to be a perfect circle, and for example, even if the shape is oval, the same effect can be obtained for the prevention of the collision of the ejected liquid droplets.

The ejection head 6 and the reservoir 7 are set in a one to one correspondence. The user attaches the flow path mouthpiece unit 2 storing the medicinal solution for ejection in the reservoir 7 to the housing case 1. Subsequently, the user operates the setting menu changeover button 11, the setting up button 12 and the down button 13, and the SET button 14, thereby to set the amount of the solution. When the user presses the ejection start button, the medicinal solution stored in the reservoir 7 is ejected toward the flow path outer wall (the inner wall of the flow path mouthpiece unit) from the surface of the structure 3 through the ejection head 6.

As an ejection head, the present embodiment uses an ejection head of a thermal ink jet type having densely located ejection ports for the fine liquid droplets. This is an ejection head having an electrothermal conversion element for heating the medicinal solution as an ejection energy generating element for ejecting the medicinal solution. According to this method, the total number of fine liquid droplets ejected per an area and per an hour can be set and controlled with high accuracy, and the total ejected liquid droplets can be controlled with high accuracy. In addition, this is a liquid ejecting unit suitable for application that requires good reproducibility.

By disposing the plurality of ejection heads, a plurality of kinds of medicines can be sprayed. At this time, by disposing the plurality of ejection heads on the structure 3 provided inside the airflow path, a plurality of solution ejection portions is operated by a single operation, thereby a plurality of kinds of medicines and a plurality of the same kinds of medicines can be sprayed by a single operation. The former, for example, sprays medicine to expand a bronchial tube and insulin to reach lung and adjust a blood-sugar level, thereby enhancing a therapeutic effect. The latter can reduce the number of times the medicine is administered to a patient who requires a large number of doses, thereby contributing to an enhancement of the QOL (Quality of Life) of the patient.

A cross-section orthogonal to the airflow of the airflow path having the structure is ring-shaped, and includes a plurality of reservoirs inside the structure, and has the plurality of ejection heads disposed on the surface of the structure. The cross-section orthogonal to the airflow may be in the shape of a closed ring of a rectangle having angular portions, but a closed ring shape having no angular portion is most preferable. In the case of the cross-section having no closed ring shape, a sufficient ratio of the long side to the short side can be preferably secured so that the flow rate distribution is in the form of a line instead of points.

A support to hold the structure is preferably streamline-shaped so as not to disturb the flow of the airflow. To prevent the ejected liquid droplets from colliding with each other and becoming large in liquid droplet size, an aggregation of the liquid droplets ejected from the plurality of ejection heads is preferably disposed so as not to be divided by the support when seen from the cross-section orthogonal to the ring-shaped airflow.

While the material of the flow path mouthpiece unit 2 may be an optional material, it is preferably a material selected from glass, plastic, and metal.

When a plurality of reservoirs is available, a combination of the medicinal solution and a solution of a scenting agent or a solution of a flavoring agent is possible, in addition to a combination of a plurality of medicinal solutions. A main medium of the ejected liquid is preferably the water or an organic matter, and when administered to a living body, the water is more preferably the main medium.

The medicines used in the present invention conceptually include not only the medicine of medicinal compound showing pharmacological and physiological actions, but also scenting and flavoring agents, fragrant materials, dye staffs, pigments, and the like in addition to the medical compound.

Further, the medicinal solution used for the present invention is referred to as a liquid medicine or a liquid medium containing the medicine. The medicinal solution may contain any additive. A state of the medicine in the solution may be any of dissolution, dispersion, emulsification, suspension, and slurry, and is more preferably uniformized in solution.

When the medicinal solution is used as the medicine, a main medium of the liquid is preferably the water or an organic matter, and when considering that the solution is administered to a living body, the water is preferably the main medium.

The ejecting system for the liquid droplets may be a piezo-actuator system or an ultrasonic system as the vibration system, and a thermal ink jet system with thermal energy supplied thereto as a negative pressure system. To control a plurality of liquid droplet amounts to be sprayed with high accuracy, the negative pressure system is superior to the vibration system.

Particularly, a number of liquid medicine ejection units having an ejection head based on a principle of the thermal ink jet are preferably configured to be independently driven. In selecting a system, manufacturing cost, unit price, integration density, and the like are cited as criteria, and in view of the above described two points, a system of applying thermal energy to create bubbles is more preferable.

Further, activation commands may be relayed to the plurality of liquid ejection portions to activate them sequentially in a single operation, or may be supplied simultaneously. A time lag in the relay can be arbitrarily set, and it is only necessary to set a time lag of a value larger than the time of operation of the previously operated liquid ejection portion.

Figure 4A:
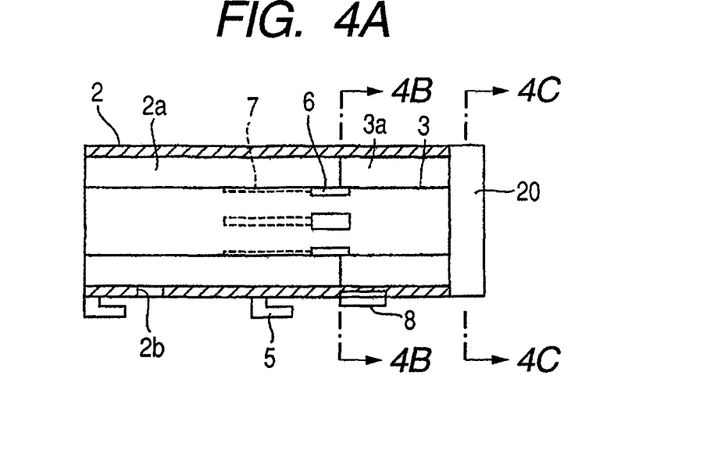
FIG. 4A is a cross-sectional view in an axial direction.
Figure 4B:
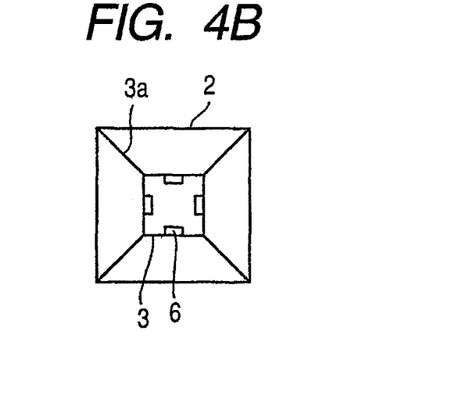
FIG. 4B is a cross-sectional view seen from the line 4B-4B of FIG. 4A.
Figure 4C:
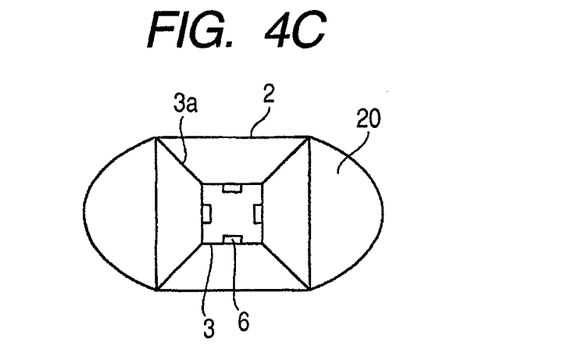
FIG. 4C is a cross-sectional view seen from the line 4C-4C of FIG. 4A.

FIGS. 4A, 4B, and 4C illustrate a second embodiment. As illustrated in FIGS. 4B and 4C, since the cross-sectional shapes of an airflow path 2a of a flow path mouthpiece unit 2 and a structure 3 are rectangular, a mouth spacer 20 is provided so that no opening is left when it is held in the mouth. The other points are the same as the first embodiment. The rectangular structure 3 storing a medicine ejection portion has an advantage of being easy in manufacture and moderate in price as compared with a circular one.

Figure 5A:
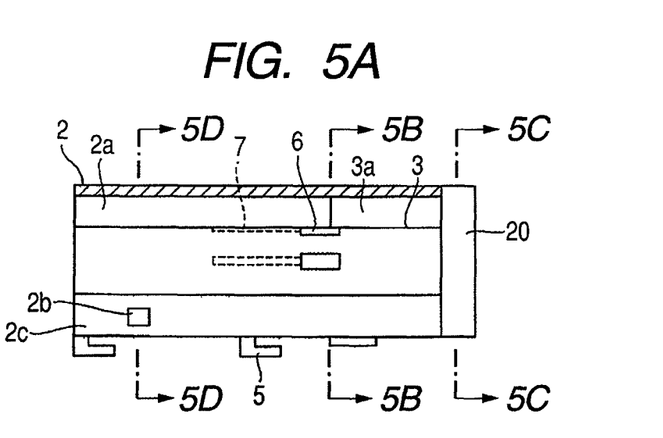
FIG. 5A is a cross-sectional view in an axial direction.
Figure 5B:
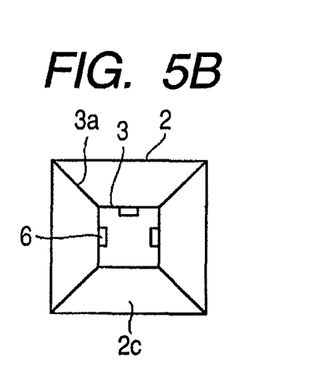
FIG. 5B is a cross-sectional view seen from the line 5B-5B of FIG. 5A.
Figure 5C:
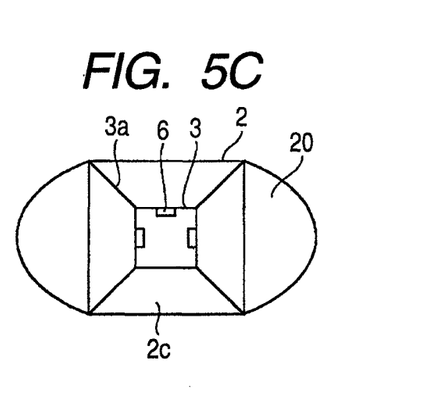
FIG. 5C is a cross-sectional view seen from the line 5C-5C of FIG. 5A.
Figure 5D:
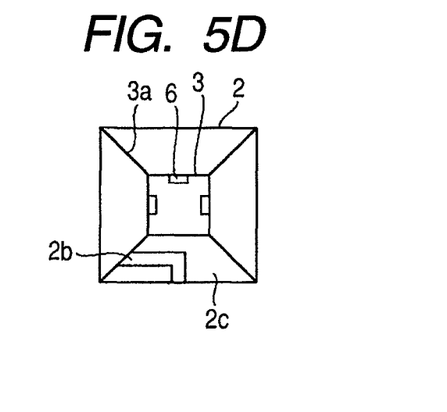
FIG. 5D is a cross-sectional view seen from the line 5D-5D of FIG. 5A.

FIGS. 5A, 5B, 5C, and 5D illustrate a third embodiment. As illustrated in FIGS. 5B, 5C, and 5D, the cross-sections of the airflow path 2a of the flow path mouthpiece unit 2 and the structure 3 are rectangular, and have a portion 2c which does not serve as an airflow path. That is, a portion serving as the flow path has a "C" shape. With a portion 2C not serving as the flow path, the electrical wiring of the ejection head 6 is facilitated. Similarly to the second embodiment, a mouth spacer 20 is provided.

As illustrated in FIG. 5D, a communication hole 2b for checking the negative pressure inside the inhalation flow path 2a is opened laterally in an L shape. Other points are the same as the first embodiment. In the third embodiment, since a pressure sensor for detecting the negative pressure generated inside the flow path by the inhalation by the user is provided, the inhalation and the ejection start can be synchronized. The user does not need to press a medicine ejection button, which enhances user convenience.

Figure 6A:
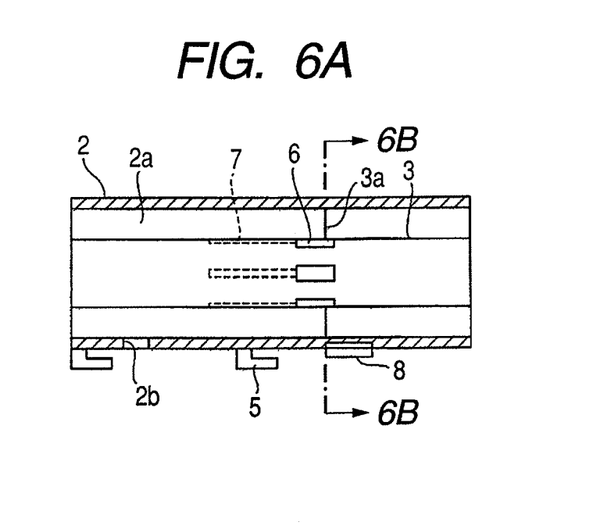
FIG. 6A is a cross-sectional view in an axial direction.
Figure 6B:
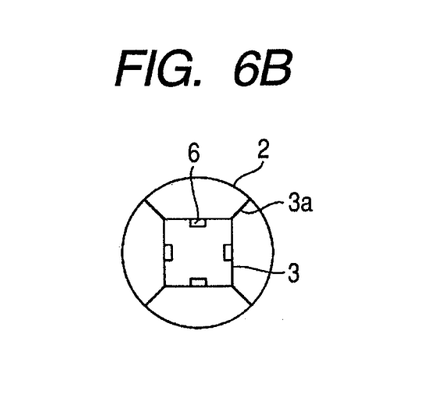
FIG. 6B is a cross-sectional view seen from the line 6B-6B of FIG. 6A.
Figure 7A:
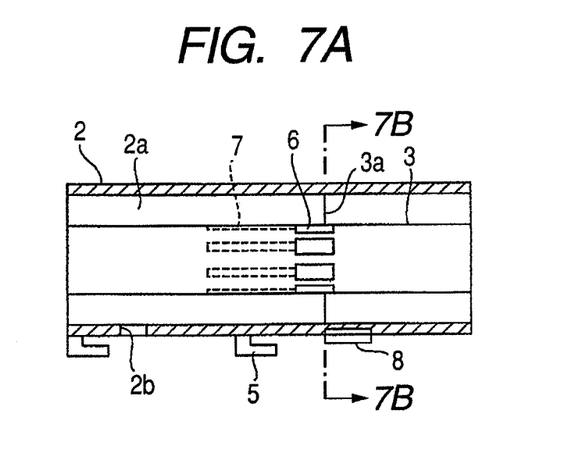
FIG. 7A is a cross-sectional view in an axial direction.
Figure 7B:
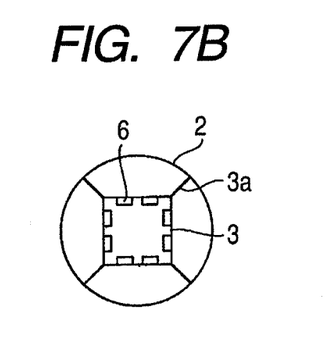
FIG. 7B is a cross-sectional view seen from the line 7B-7B of FIG. 7A.

FIGS. 6A and 6B illustrate a fourth embodiment. The cross-section of an airflow path 2a is circular, and the cross-section of a structure 3 is rectangular and closed. FIGS. 7A and 7B illustrate a fifth embodiment. Depending on the size of the structure 3 and the size of an ejection heads 6, it is possible to dispose a plurality of ejection heads 6 on one side of the structure 3. The ejection head 6 and a reservoir 7 are connected in a one to one correspondence. Other points are the same as the first embodiment.

Figure 8A:
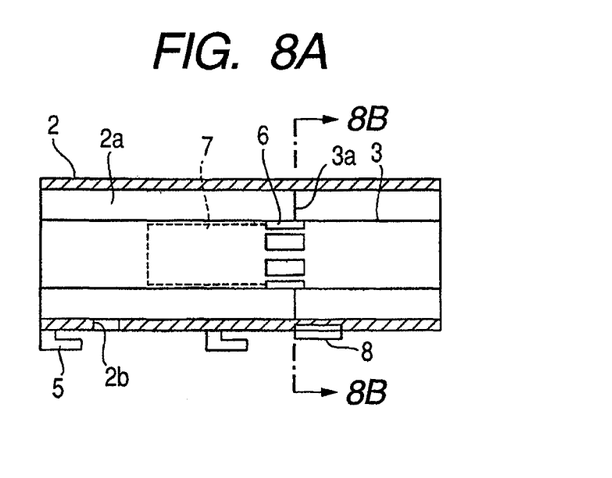
FIG. 8A is a cross-sectional view in an axial direction.
Figures 8B, 8C:
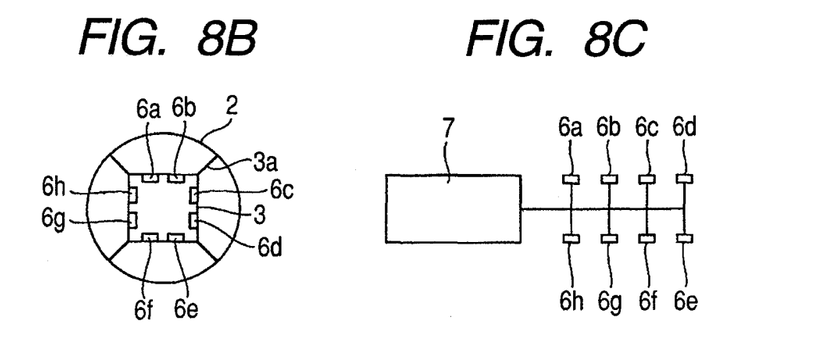
FIG. 8B is a cross-sectional view seen from the line 8B-8B of FIG. 8A.
FIG. 8C is a piping diagram.

FIGS. 8A, 8B, and 8C illustrate a sixth embodiment. In this case, a medicinal solution is supplied to a plurality (eight pieces) of ejection heads 6a to 6h from one reservoir 7. FIG. 8C illustrates a piping diagram of the reservoir 7 and the ejection heads 6a to 6h. Since each of the ejection heads 6a to 6h ejects the liquid by thermal energy or vibration energy, the liquid can be held by surface tension of the ejection ports of the ejection heads 6a to 6h, even if a stop valve is not provided between the reservoir 7 and the medicine ejection portion.

Since it is possible to eject the same medicinal solution from the plurality of ejection heads, this is suitable for inhalation by aged persons and by infants, whose breathing is shallow.

Figure 9A:
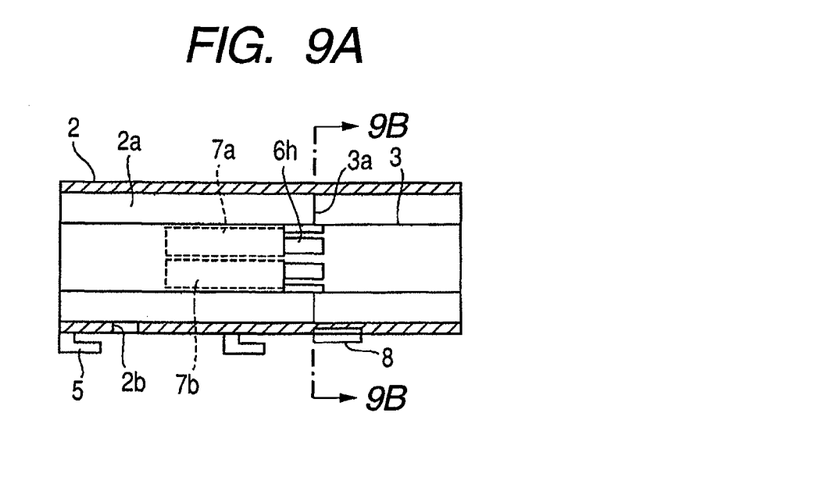
FIG. 9A is a cross-sectional view in an axial direction.
Figure 9B:
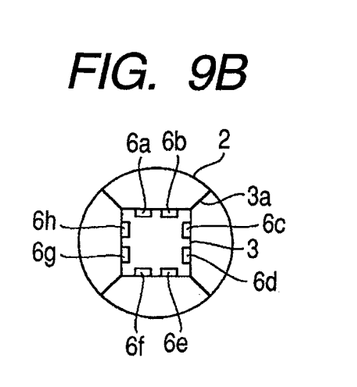
FIG. 9B is a cross-sectional view seen from the line 9B-9B of FIG. 9A.
Figure 9C:
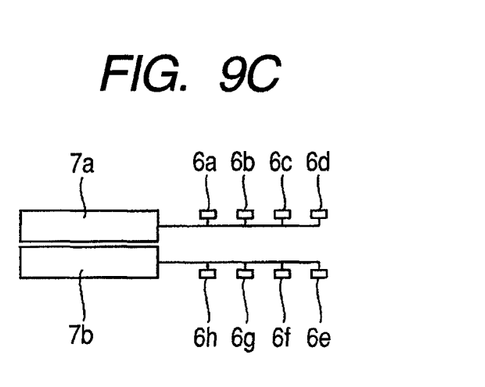
FIG. 9C is a piping diagram.

FIGS. 9A, 9B, and 9C illustrate a seventh embodiment. This supplies a medicinal solution to a plurality (eight pieces) of ejection heads 6a to 6h from two reservoirs 7a and 7b. FIG. 9C is a view illustrating reservoirs 7a and 7b and the piping of ejection heads 6a to 6h. In the present embodiment, a combination of the medicinal solution and a scenting agent or the liquid of a flavoring agent is also possible in addition to a combination of the plurality of medicinal solutions, and this has an effect of reducing difficulties of dosage for the patient.

Figure 10A:
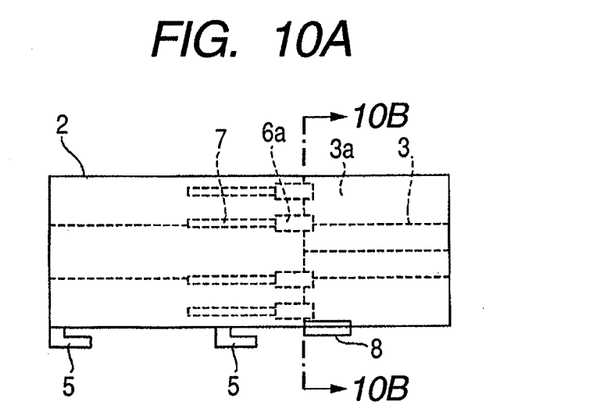
FIG. 10A is a cross-sectional view in an axial direction.
Figure 10B:
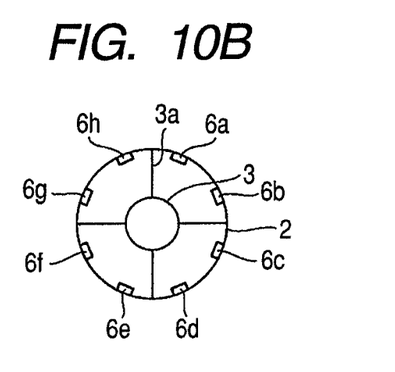
FIG. 10B is a cross-sectional view seen from the line 10B-10B of FIG. 10A.

FIGS. 10A and 10B illustrate a seventh embodiment. In the present embodiment, a plurality of ejection heads 6a to 6h is disposed from the outer wall of an airflow path to a structure 3 so as to eject medicinal solutions. The ejection heads 6a to 6h are connected to the reservoir 7 in a one to one correspondence.

(Preferred Embodiment of Structure 3)

Figure 12A:
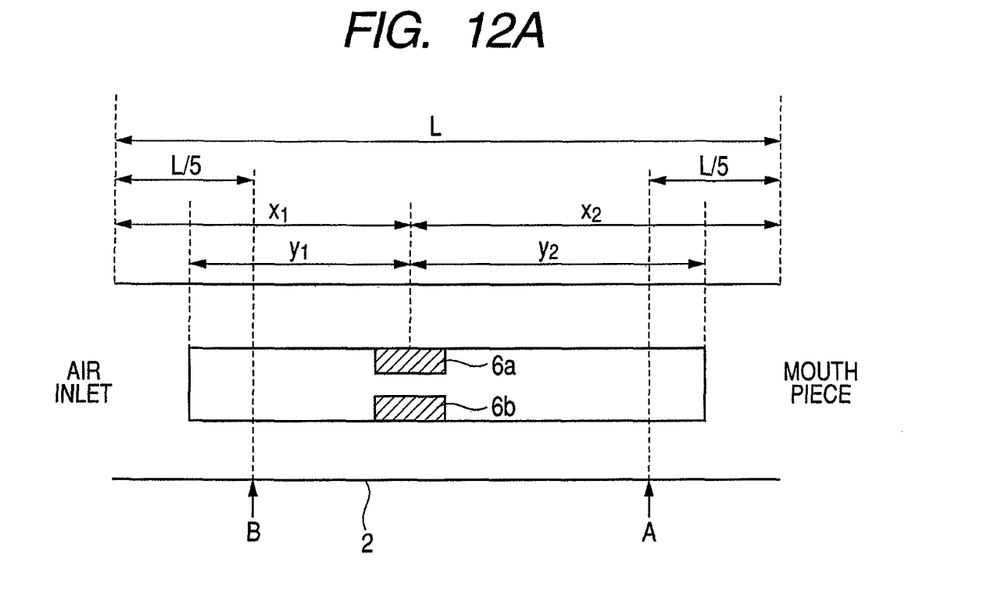
FIG. 12A is a schematic cross-sectional view of the airflow path for describing the positional relationship among the airflow path, the structure and the ejection head.
Figure 12B:
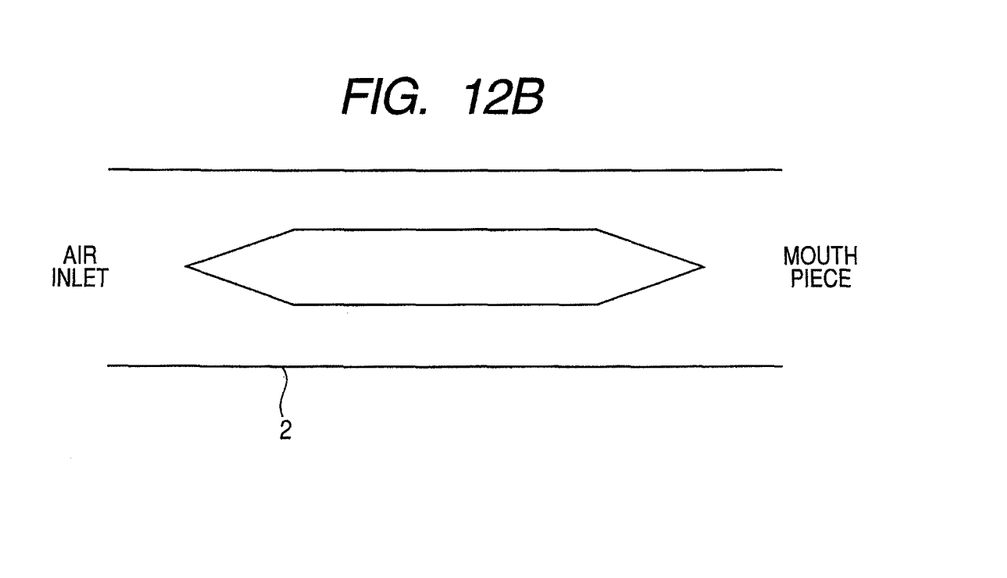
FIG. 12B is a schematic cross-sectional view of the airflow path when the end portion of the structure is cone-shaped.

Here, to realize the prevention of the collision of the liquid droplets, which is the advantage of the present invention, an embodiment of a preferred structure will be described with reference to FIGS. 12A and 12B. Hereinafter, when referred to as "position of an ejection head 6", it means a position in the airflow directions (the left and the right directions of FIG. 12A) in an airflow path.

At the position of the ejection head 6, at least the airflow path 2 and the structure 3 preferably exist. That is, the ejection head 6 is inside the airflow path 2, and moreover, is disposed in an area where the structure inside thereof stretches. Hereinafter, with the position of the ejection head 6 as a reference, an air inlet side is sometimes referred to as an upstream of the airflow, and the mouthpiece side as a downstream of the airflow.

A preferred relationship between the structure 3 end and the airflow path 2 in the downstream side of the airflow will be described. It is most desirable that the structure 3 is definitely located upstream of the airflow path 2 so that the end portion of the structure 3 matches the end portion of the airflow path 2. When the structure 3 is located partway inside the airflow path 2, assuming that the length of the airflow path 2 is L, it is preferable that the end portion of the structure is located at the mouthpiece side rather than at the spot (spot A of FIG. 12A) inside L/5 from the end portion of the airflow path 2. This is because, when an end of the structure 3 is located inward from spot A, the liquid droplets ejected from the plurality of ejection heads likely join together before reaching the mouthpiece, depending on the flow rate of the airflow. Although it does not matter even if the end portion of the structure 3 is put outside from the end portion of the airflow path 2, that is, the structure 3 is projected outside the mouthpiece 4, such projection must be to the extent of not disturbing the inhalation by the user. A projection length of the structure 3 is preferably about L/10.

With respect to the preferred positional relationship between the end portion of the structure 3 and the airflow path 2 in the upstream side of the airflow, though there is any particular restriction imposed, it is preferably the same as the downstream side. In this case, the position corresponding to spot A is a spot B.

Next, a preferred position of the ejection head 6 will be described. In connection with the upstream side of the airflow, either one or both of a distance x1 from the end portion of the airflow path 2 to the ejection head 6 and a distance y1 from the end portion of the structure 3 to the ejection head 6 are preferably larger than L/5. This is because a turbulence of the airflow is likely to occur near the air inlet and the end portion of the structure, and when the ejection head is located at such positions, the liquid droplets are likely to be thrown into turbulence.

Similarly, in connection to the downstream side of the airflow, either one or both of a distance x2 from the end portion of the airflow path 2 to the ejection head 6 and a distance y2 from the end portion of the structure 3 to the ejection head 6 are preferably larger than L/5.

When the structure 3 is provided only in the inside of the airflow path, as illustrated in FIG. 12B, from among the end portions in front and rear of the structure, either one or both are preferably cone-shaped instead of being columnar in shape. This is because, when seen by the cross-section which is orthogonal to the airflow in this manner, in proportion as the cross-sectional area of the structure 3 comes up to the end portion of the airflow path, if an attempt is made to reduce the area in stages, it is hard for the turbulence of the airflow to arise at the end of the structure 3.

(Positions of a Plurality of Ejection Heads)

It is not preferable that the plurality of ejection heads are so provided in upstream and downstream portions of the airflow as to be located at the same positions when seen by the cross-section orthogonal to the airflow of the airflow path. This is because the liquid droplets ejected from the plurality of ejection heads pass through the same airflow. As shown in the embodiments so far, the positional relationship by which the plurality of ejection heads are disposed is preferably in positions shifted from each other when seen by this crosssection. Most preferably, the ejection heads are provided symmetrically at equal intervals when seen from this cross-section.

In the first to the seventh embodiments, a specific example of adjustment and measuring method of the ejected liquids will be described.

First, two kinds of a dissolving solution for dissolving the medicine was prepared. The content thereof is shown below. By selecting the dissolving solution according to the medicine, ejection liquids were prepared.

by recovering the ejection liquid droplet and using a high speed liquid chromatograph (LC-2000: made by JASCO corporation), an analytical curve by concentration was prepared in advance for each matter, and the concentrations of the above described two matters were measured and identified. As an determination reference, those whose liquid droplet size is the difference between the value immediately after the ejection and the value measured at the outlet of the mouthpiece 4 and is within ±0.2 μm and whose concentration is within 0.2 percent were determined as OK. The measurement result is shown in Table 1.

TABLE 1

| Embodiment | Kind of Medicinal solution | Combination of Medicine ejection portion | Liquid Droplet size | Concentration | Determination |
|---|---|---|---|---|---|
| 1 | Insulin | Any two pieces | 3.0 | 0.4 | OK |
| | | Any three pieces | 3.0 | 0.4 | OK |
| | | Four pieces | 3.0 | 0.4 | OK |
| 2 | Insulin | Any two pieces | 3.0 | 0.4 | OK |
| | | Any three pieces | 3.0 | 0.4 | OK |
| | | Four pieces | 3.1 | 0.4 | OK |
| 3 | Insulin | Any two pieces | 3.0 | 0.4 | OK |
| | | Any three pieces | 3.0 | 0.4 | OK |
| 4 | Insulin | Any two pieces | 3.0 | 0.4 | OK |
| | | Any three pieces | 3.0 | 0.4 | OK |
| | | Four pieces | 3.1 | 0.4 | OK |
| 5 | Insulin | Any two pieces on different sides | 3.0 | 0.4 | OK |
| | | Any two pieces on the same side | 3.1 | 0.4 | OK |
| | | Any four pieces | 3.1 | 0.4 | OK |
| | | Eight pieces | 3.1 | 0.4 | OK |
| 6 | Insulin | Any two pieces on different sides | 3.0 | 0.4 | OK |
| | | Any two pieces on the same side | 3.1 | 0.4 | OK |
| | | Any four pieces | 3.0 | 0.4 | OK |
| | | Eight pieces | 3.0 | 0.4 | OK |
| 7 | Reservoir A: Insulin Reservoir B: DPP4 Inhibitor | 6a, 6e | 3.0/3.1 | 0.4, 0.1 | OK |
| | | 6a, 6b, 6e, 6f | 3.1/3.1 | 0.4, 0.1 | OK |
| | | 6a, 6b, 6c, 6e, 6f, 6g | 3.0/3.1 | 0.4, 0.1 | OK |
| | | Eight pieces | 3.0/3.1 | 0.4, 0.1 | OK |
| 8 | Insulin | Any two pieces on different sides | 3.0 | 0.4 | OK |
| | | Any two pieces on the same side | 3.1 | 0.4 | OK |
| | | Any four pieces | 3.0 | 0.4 | OK |
| | | Eight pieces | 3.0 | 0.4 | OK |

Shown liquid droplet size in seventh embodiment represents A/B

| Liquid A: Arginine hydrochloride salt | 10 mg/ml Aqueous solution |
|---|---|
| Liquid B: Benzalkonium chloride | 10 mg/ml Aqueous solution |

| Kind of Medicinal Solution | Dissolving Solution | Setting Concentration | Droplet size |
|---|---|---|---|
| INSULIN | A | 0.4% | 3.0 |
| DPP4 INHIBITOR | B | 0.1% | 3.1 |

In each of the embodiments, the required ejection liquid was stored in the reservoir and under the condition of a predetermined voltage, frequency, and duty (a ratio of time by which the voltage is applied in the time of one cycle), the liquid was ejected. By using a droplet size distribution meter (Spraytec: made by Malvern Instruments Ltd), the droplet size distribution of the ejection liquid was measured. Further, From Table 1, it is found that the droplet size and the concentration are maintained in any combination when a plurality of liquids is ejected at the same time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2007-142808, filed May 30, 2007, and No. 2008-121816, filed May 8, 2008, which are hereby incorporated by reference herein in their entirety.

What is claimed is:

1. An inhaler for ejecting a medicine to allow a user to inhale the same, comprising:
   a suction port for the user to inhale the medicine;
   an airflow path with length L whose first end is connected to said suction port and whose second end has an air inlet, said airflow path guiding the medicine to said suction port by an airflow generated by inhalation by the user;

a plurality of medicine ejection portions configured to eject the medicine to said airflow path; and a structure inside said airflow path, and having an end portion, wherein said end portion of said structure is positioned less than L/5 from said first end of said airflow path, and wherein said plurality of medicine ejection portions are positioned by more than L/5 apart from said second end of said airflow path and from said end portion of said structure.

2. The inhaler according to claim 1, further comprising a plurality of reservoirs and wherein a medicinal solution is supplied to each of said plurality of medicine ejection portions from said plurality of reservoirs.

3. The inhaler according to claim 2, wherein different medicinal solutions are stored in respective ones of said reservoirs.

4. The inhaler according to claim 1, wherein said airflow path has an annular cross-section in which said structure is disposed.

5. The inhaler according to claim 1, further comprising a reservoir storing the medicine and disposed inside said structure, and wherein said plurality of medicine ejection portions is disposed on a surface of said structure.

6. The inhaler according to claim 1, wherein each of said plurality of medicine ejection portions has an ejection head for ejecting the medicine by supplying thermal energy or vibration energy.

7. The inhaler according to claim 1, wherein each of said plurality of medicine ejection portions is disposed on an outer wall of said airflow path.

8. The inhaler according to claim 1, wherein said structure extends from a position at which said plurality of medicine ejection portions is disposed toward said suction port.

9. The inhaler according to claim 1, wherein said structure has such shape that the maxima of an air flow rate does not gather at one point, but is dispersed inside of said airflow path.

10. The inhaler according to claim 1, wherein said end portion of said structure is cone-shaped.

* * * * *